(12) United States Patent
Solymar et al.

(10) Patent No.: US 6,949,116 B2
(45) Date of Patent: *Sep. 27, 2005

(54) DEVICE FOR PLUGGING AN OPENING SUCH AS IN A WALL OF A HOLLOW OR TUBULAR ORGAN INCLUDING BIODEGRADABLE ELEMENTS

(75) Inventors: Laszlo Solymar, Billdal (SE); Daniel Thomas Thommen, Zug (CH); Jerome Bernhard, Zürich (CH)

(73) Assignee: Carag AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/306,481

(22) Filed: Nov. 27, 2002

(65) Prior Publication Data

US 2003/0149463 A1 Aug. 7, 2003

Related U.S. Application Data

(63) Continuation-in-part of application No. 09/707,691, filed on Nov. 7, 2000, now Pat. No. 6,488,706, which is a continuation-in-part of application No. 09/180,379, filed as application No. PCT/SE97/00747 on May 6, 1997, now abandoned.

(30) Foreign Application Priority Data

May 8, 1996 (SE) ................................................ 9601752

(51) Int. Cl.$^7$ ................................................ A61F 2/06
(52) U.S. Cl. ...................................... 623/1.12; 623/1.16
(58) Field of Search ................................ 606/200, 214, 606/213, 215–218, 192, 151; 604/104; 623/3.1, 3.16, 3.13, 3.17, 3.18

(56) References Cited

U.S. PATENT DOCUMENTS 2,849,002 A 8/1958 Oddo ........................ 128/325
4,512,338 A 4/1985 Balko et al. .................... 128/1

(Continued)

FOREIGN PATENT DOCUMENTS

DE 2514142 10/1976
DE 2822603 11/1979

(Continued)

OTHER PUBLICATIONS

Agrawal et al., Deformation Characteristics of a Bioabsorbable Intravascular Stent, Investigative Radiology, Dec. 1992, 1020–1024, vol. 27.

(Continued)

*Primary Examiner*—Corrine McDermott
*Assistant Examiner*—Hieu Phan
(74) *Attorney, Agent, or Firm*—Baniak Pine & Gannon

(57) ABSTRACT

An implant for occluding a passage in a circulatory system is provided. The implant in one form includes a plurality of thin wire-like members each having a proximal and a distal end and a first holder to which the distal ends of the members are attached. The proximal ends of the members are attached to a second holder. The implant includes an expansible occluding body attached to the members at a point intermediate the first and second holders. A carrier rod is releasably attached to the first holder and upon which the second holder is slidably received. A driving implement is located on the carrier rod, the driving implement contacting the second holder and movable toward the first holder along the carrier rod. The members are attached to the first and second holders in a manner to cause the members to execute a twisting motion relative to the longitudinal axis to yield a plurality of generally radially extending loops combining to form a first fixation structure adjacent the distal face of the occluding body, and a second fixation structure of generally radially extending loops adjacent the proximal face of the occluding body. In another form, the implant includes a balloon structure which is expanded from within by a spring-like mechanism in situ, or by the foregoing radially extending loop mechanism.

16 Claims, 6 Drawing Sheets

U.S. PATENT DOCUMENTS

| | | | |
|---|---|---|---|
| 5,334,210 A | | 8/1994 | Gianturco .................... 606/151 |
| 5,433,727 A | | 7/1995 | Sideris |
| 5,733,294 A | * | 3/1998 | Forber et al. ................ 606/151 |
| 5,980,564 A | | 11/1999 | Stinson .......................... 623/1 |
| 6,183,496 B1 | * | 2/2001 | Urbanski .................... 606/213 |
| 6,245,103 B1 | | 6/2001 | Stinson ..................... 623/1.22 |
| 6,270,515 B1 | | 8/2001 | Linden et al. |
| 6,287,318 B1 | | 9/2001 | Villar et al. ................. 606/191 |
| 6,287,344 B1 | | 9/2001 | Wampler et al. .......... 623/23.72 |
| 6,315,787 B1 | * | 11/2001 | Tsugita et al. .............. 606/213 |
| 6,350,270 B1 | * | 2/2002 | Roue .......................... 606/151 |
| 6,355,052 B1 | | 3/2002 | Neuss et al. |
| 6,432,134 B1 | | 8/2002 | Anson et al. |
| 6,454,780 B1 | * | 9/2002 | Wallace ...................... 606/151 |
| 6,488,706 B1 | * | 12/2002 | Solymar ....................... 623/3.1 |
| 6,702,834 B1 | * | 3/2004 | Boylan et al. .............. 606/200 |

FOREIGN PATENT DOCUMENTS

| | | | |
|---|---|---|---|
| EP | 0 350 043 | 1/1990 | ............. A61F/2/02 |
| EP | 0 362 113 B1 | 4/1990 | |
| EP | 0 927 540 A1 | 7/1999 | ........... A61B/17/12 |
| FR | 2714284 | 6/1995 | |
| WO | WO 96/01591 | 1/1996 | ........... A61B/17/22 |
| WO | WO 97/28744 | 8/1997 | ........... A61B/17/00 |
| WO | WO 02/38051 A2 | 5/2002 | ........... A61B/17/00 |
| WO | WO 02/053202 A1 | 7/2002 | ........... A61L/31/02 |

OTHER PUBLICATIONS

Weiler et al., Enhancement of the Mechanical Properties of Polylactides by Solid–State Extrusion, Biomaterials, 529–535, vol. 17 No. 5.

* cited by examiner

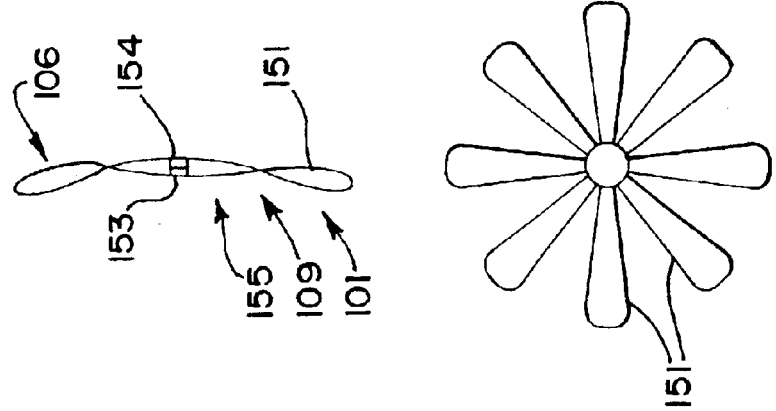
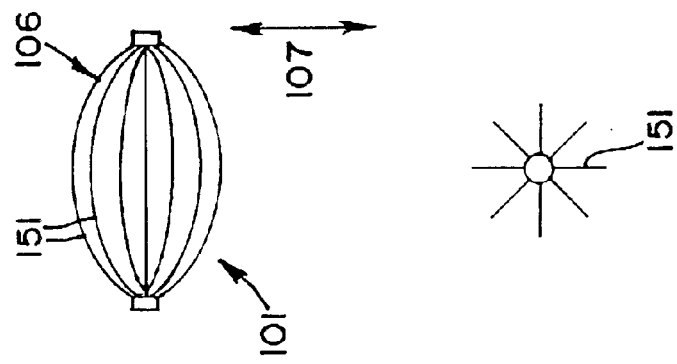
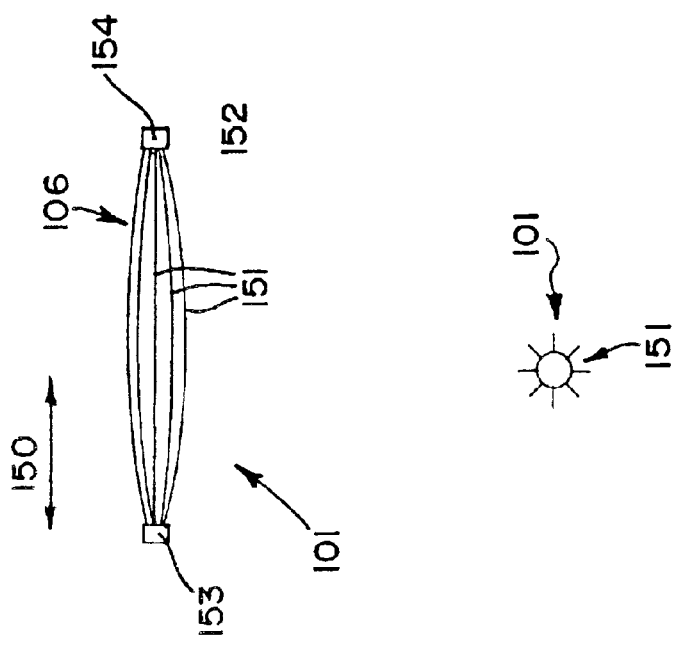

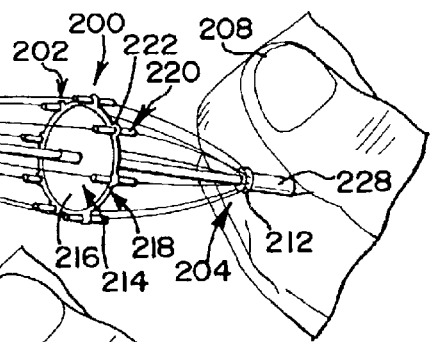
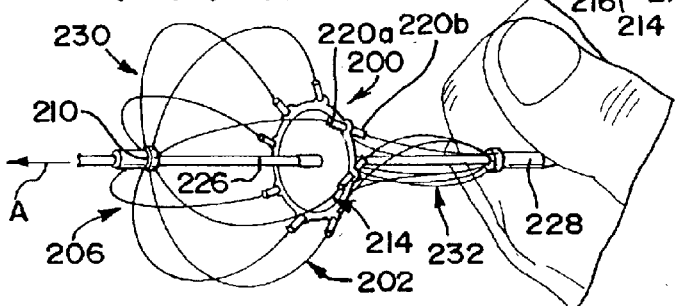
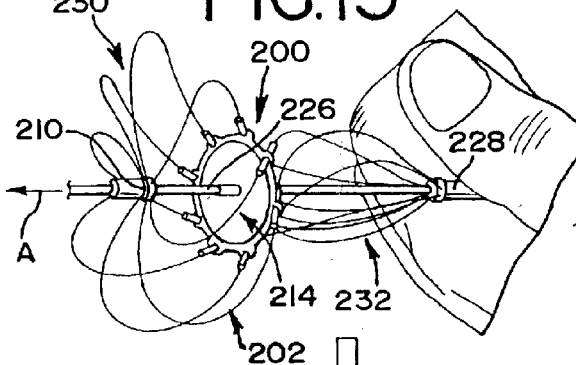
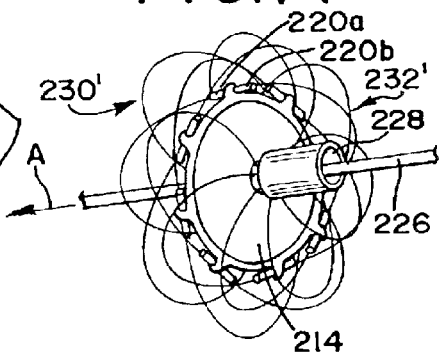
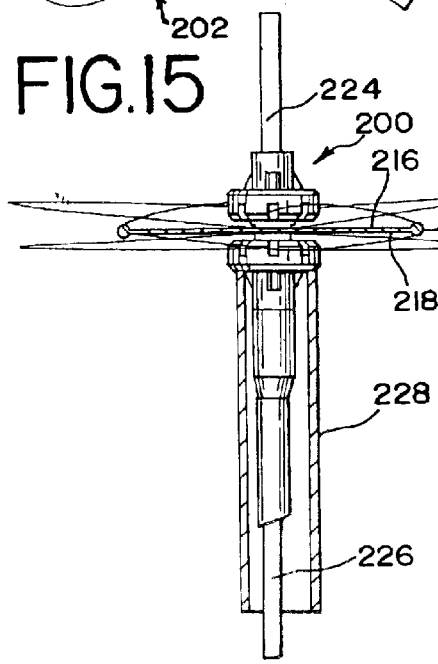
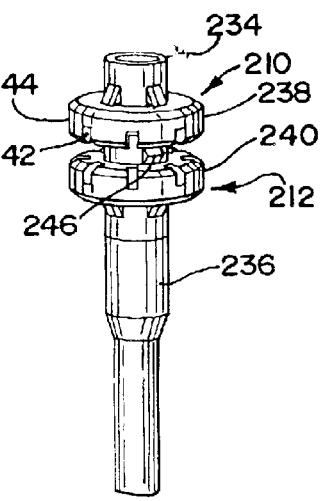

DEVICE FOR PLUGGING AN OPENING SUCH AS IN A WALL OF A HOLLOW OR TUBULAR ORGAN INCLUDING BIODEGRADABLE ELEMENTS

APPLICATION HISTORY

This application is a continuation-in-part of U.S. patent Ser. No. 09/707,691 filed Nov. 7, 2000, now U.S. Pat. No. 6,488,706, issued Dec. 3, 2002, which is a continuation-in-part of U.S. Ser. No. 09/180,379 filed Nov. 6, 1998, now abandoned, which claims priority to PCT/SE97/00747 filed May 6, 1997, and to Sweden 9601752-0 filed May 8, 1996.

FIELD OF THE INVENTION

The present invention generally relates to an implant device for closing a body passage (e.g., an aperture through the auricle diaphragm or the ventricle diaphragm of a heart) or in a body channel, and more particularly comprising an occluding or closing body which is expanded and fixed into place at the passage area to be occluded/closed. In one embodiment, the implant device may be entirely or partly biodegradable.

BACKGROUND OF THE INVENTION

By way of example EP 0 362 113 B1 shows a device for closing a passage in the heart of patients, wherein the closing part runs the risk of tipping over and thereby causing the passage to be exposed in passing through the heart. The cause of the nonsecure closing capacity is the relative unfixed maneuverability for the closing part when applied around the passage, and that the application takes part long before it has arrived in its final position around the passage in the heart.

The main object of the present invention is therefore primarily to try to solve the described problem with maneuverability and application of the device.

SUMMARY OF THE INVENTION

The foregoing object is achieved by means of a device according to the present invention, which is substantially characterized in that a fluid tight closing body that expands and stiffens in a radial direction is arranged to be built up or otherwise assembled at the position of the intended closing spot, after insertion through a body vein.

The present invention provides an implant for occluding a passage in a circulatory or like system. The implant in one embodiment includes a plurality of thin stiff generally inextensible members each having a proximal and a distal end and a first holder to which the distal ends of the members are attached. The proximal ends of the members are attached to a second holder. The implant includes an expansible occluding body attached to the members at a point intermediate the first and second holders. The occluding body has a distal and a proximal face.

A carrier rod is releasably attached to the first holder and upon which the second holder is slidably received. The plurality of members with the occluding body form an elongated article extending along a longitudinal axis adapted for insertion through an intravenous delivery mechanism in an insertion condition. A driving implement is located on the carrier rod, the driving implement contacting the second holder and movable toward the first holder along the carrier rod. The members are attached to the first and second holders at respective ends and at a mid-span to the occluding body in a manner to cause the members to execute a twisting motion relative to the longitudinal axis to yield a plurality of generally radially extending loops combining to form a first fixation structure adjacent the distal face of the occluding body, and a second fixation structure of generally radially extending loops adjacent the proximal face of the occluding body. The first and second fixation structures may twist into a plurality of helical loops that are oriented in opposite directions from each other. A locking element may fix the first and second attachment members in a final occluding condition upon being driven together by the driving implement.

In another embodiment, the invention is also an implantable device for closing a portion of the circulatory system comprising a closing body fixable at a passage, the closing body being a fluid occlusive body which is expandable and stiffenable in a radial direction. The closing body is located at a position in the circulatory system, and is an inflatable balloon of thin and nonthrombogenic material. In one form the foregoing threads and movable holders are used to expand the balloon in situ. In another, the balloon is a double balloon having a connection part between the two balloons arranged and constructed to form a guide for the balloon elements around the circumferential edge of the passage. A coil spring is received in a respective balloon chamber for dilating the balloon chamber in its final position.

In yet another embodiment, any of the occlusive devices shown or described herein may be formed entirely or partly of biodegradable or bioabsorbable material(s) as will be set forth in more detail below.

These and other advantages and objects achieved by the present invention will be further appreciated and understood upon consideration of the following detailed description of certain embodiments taken in conjunction with the drawings in which:

BRIEF DESCRIPTION OF THE DRAWINGS

FIGS. 3–5 relate to a first embodiment of an implant, wherein FIG. 3 shows the implant moved into position before fixing;

FIG. 4 shows the implant below a fixing position;

FIG. 5 shows the implant in its fixing position;

FIGS. 7–16 relate to a second embodiment of an implant, wherein

FIG. 7 shows an initial position for the implant seen from the side and from one end respectively;

FIG. 8 shows the implant at a between position during extension seen from the side and one end respectively;

FIG. 9 shows the implant completely extended seen from the side and one end respectively;

FIG. 10 shows schematically the principle for building up the hub and connection of the implant to it and the final position of the implant in completely extended condition seen from the side;

FIG. 11 shows the second embodiment of the present invention in another perspective view in an initial position;

FIG. 12 shows the implant of FIG. 11 in a perspective view in a first partially deployed position;

FIG. 13 shows the implant of FIG. 11 in a perspective view in a second partially deployed position;

FIG. 14 shows the implant of FIG. 11 in a perspective view in a fully deployed condition;

FIG. 15 shows the implant of FIG. 11 in a side view in a fully deployed condition; and FIG. 16 shows an enlarged perspective view of a portion of the implant, without the membrane and loops, detailing the locking hubs.

DETAILED DESCRIPTION OF EMBODIMENTS OF THE INVENTION

Figure 1:
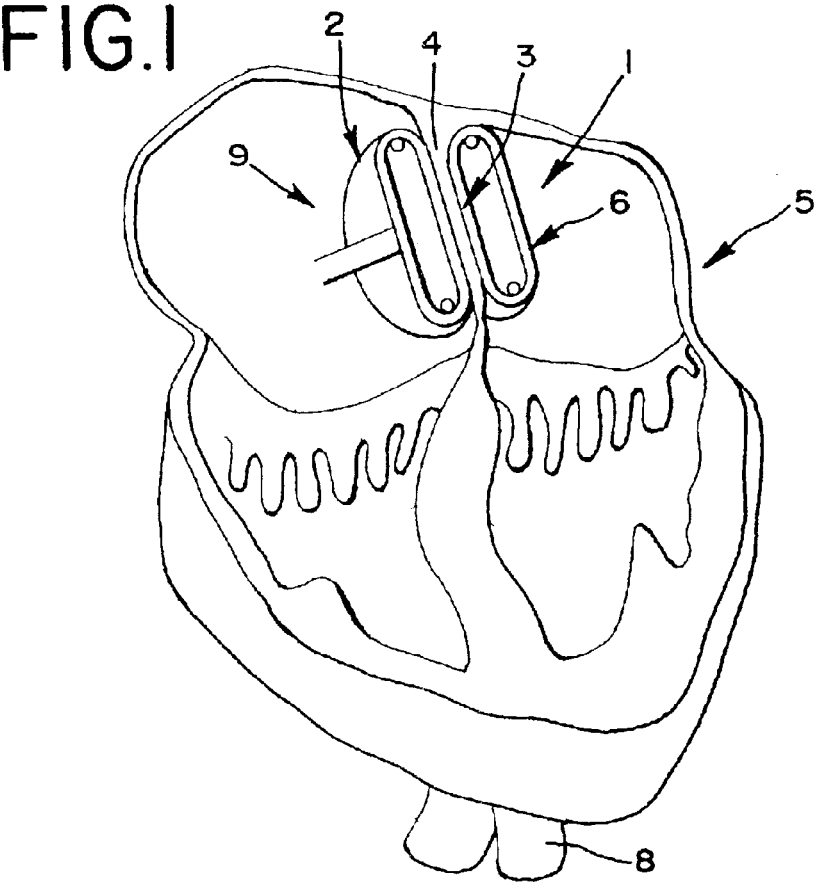
FIG. 1 shows a section through a heart during application of the implant in it.
Figure 2:
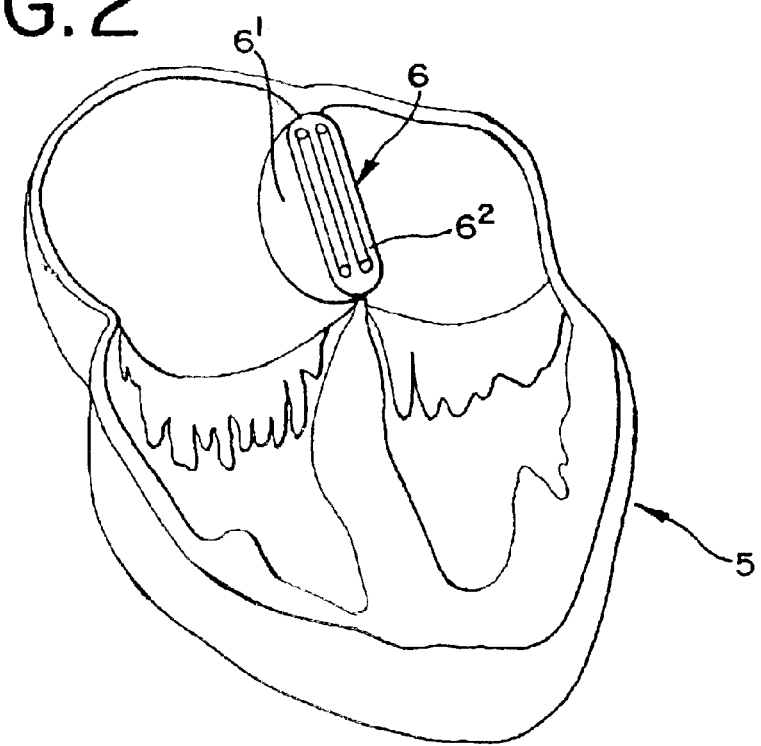
FIG. 2 shows the implant positioned in the heart.

The invention has found particular application as a cardiological implant by means of which it is possible, for example, to close an aperture through the auricle diaphragm or the ventricle diaphragm of a heart.

The implant according to the present invention is arranged to be deployed or built up (i.e., assembled) at a desired location in the body (e.g., the heart), in contrast to known implants (e.g., so-called umbrellas and sails) that are instead extended as soon as the compressed umbrella leaves its insertion sheath.

According to the invention, a device 1 is employed as an implant 2 for closing an internal passage 3, for example, an aperture in the auricle diaphragm 4 or the ventricle diaphragm of a heart 5, or in a desired body channel which one wishes to close. A closing body 6 is deployed or built up at the location. More particularly, an embodiment of the invention that is shown on the drawings in FIGS. 1–5, is formed in a radial direction 7 of expanding and stiffening fluid tight closing body 6. This body 6 is arranged to be built up at the position 9 of the intended closing spot, after insertion through a body vein 8.

The closing body 6 in this first embodiment consists of an inflatable balloon, preferably a double balloon of thin and non-thrombogenic material. A connection part 10 between the two balloon elements 6A, 6B is arranged to form a guidance for the two balloon elements 6A, 6B around the peripheral edge 3A of aperture 3.

Figure 4:
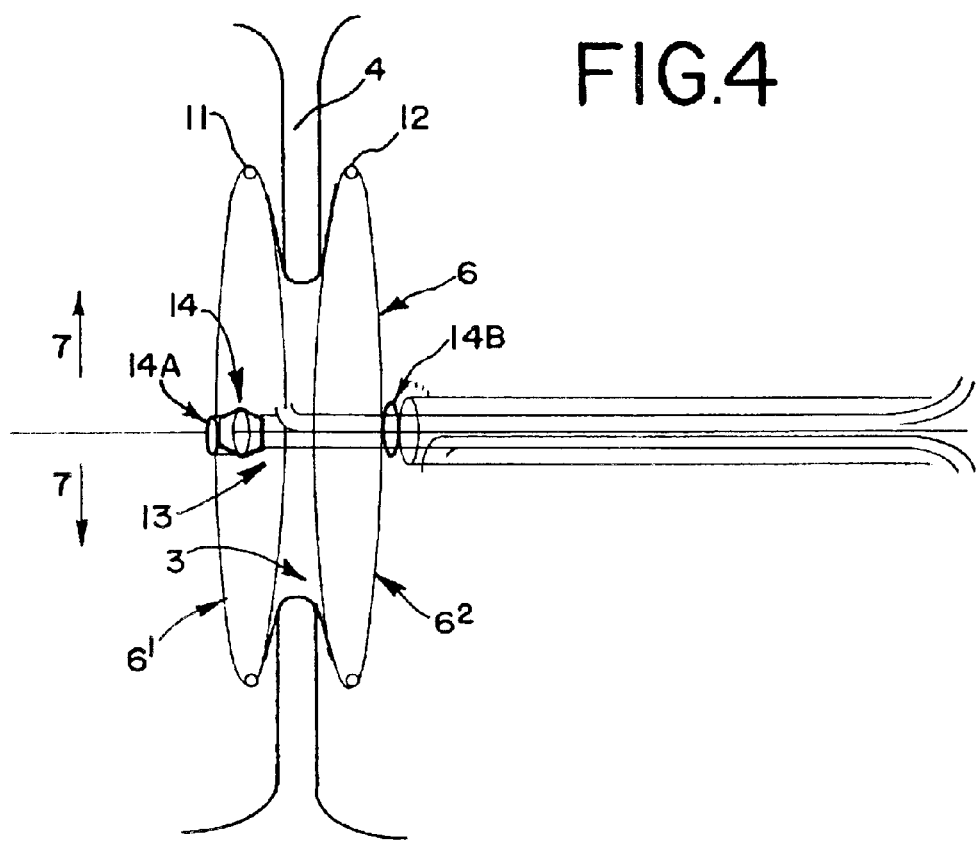
Figure 5:
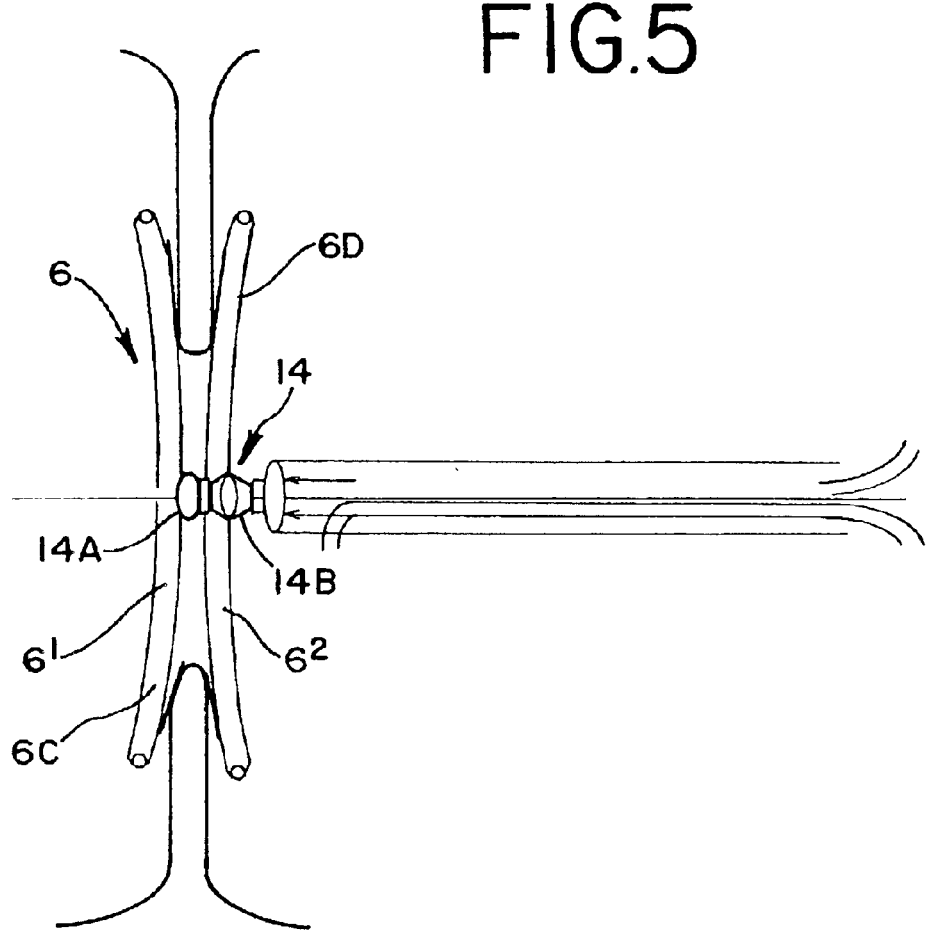
Figure 6:
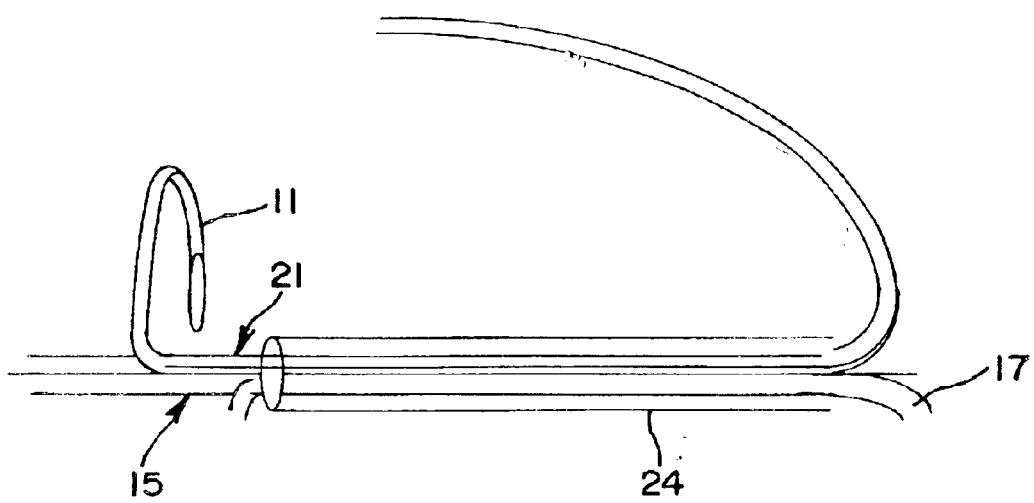
FIG. 6 shows application of a spiral thread via sheaths.
Figure 8A:
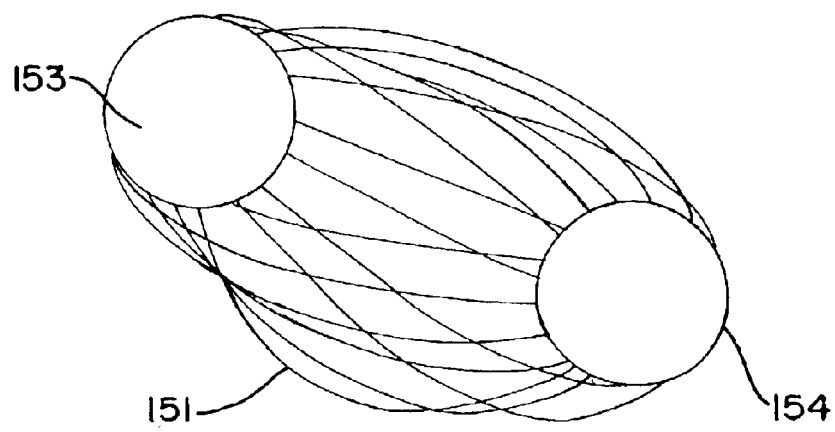
FIG. 8A shows the implant in a perspective view during extension.

Both chambers 6A, 6B of the balloon 6 are arranged to be dilated (expanded) radially 7 by means of a number of stiffening means 11, 12 which in the first shown example is realized in the shape of a coil spring, which in each case is received in the respective balloon chamber $6^1$, $6^2$, in order to dilate the balloon chamber $6^1$, $6^2$ radially in the operational position and thereby bring about an efficient holding of the balloon around the aperture 3, as is shown in FIG. 4.

Centrally at the middle 13 of the balloon is located a locking mechanism 14, which is arranged to mutually interconnect both balloon chambers $6^1$, $6^2$ at their central part. Suitably, the aforementioned locking mechanism 14 is divided into two parts, with each respective locking member 14A, 14B attachable to the outer wall 6C, 6D of the respective balloon chamber $6^1$, $6^2$. For example, the aforementioned locking members 14A, 14B may be of a prior art type, e.g., as snap together members.

The described implant 2 is delivered to the location for application in the form of a tightly rolled up double balloon 6 of thin, durable and physically friendly non-thrombogenic material over an inner sheath 15. Two narrow delivery catheters 16, 17 extend through the inner sheath 15, of which the distal delivery catheter 16 has its outlet opening 18 in the distal balloon $6^1$ and in a corresponding manner, the proximal catheter 17 has its outlet opening 19 in the proximal balloon $6^2$.

Figure 3:
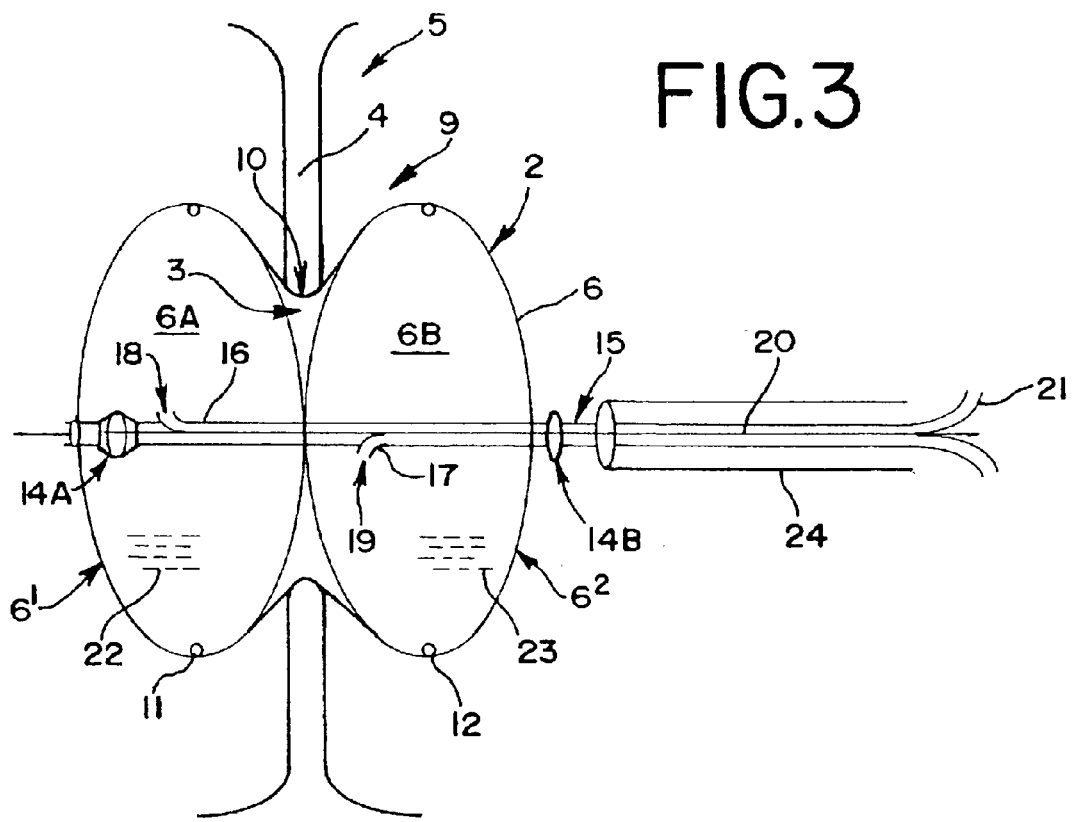

By means of the well-known Seldinger technique, a vein inserter of dimension 11F is inserted into the femoral vein. A catheter is placed in the left upper pleural vein, and through this is passed a conductor 20 which is left behind for subsequent implant work. At the same time, this constitutes a part of a safety system against unintentional release, because the conductor 20 locks the fastening mechanism between the inner sheath 15 and the implant 2. Over the conductor 20, the implant 2 is introduced into the vein inserter, then in the lower vena cava and further up to the heart 5 until the central mark reaches the middle of the aperture 3, or any other defect which is desired to be closed. After that, the distal balloon $6^1$ is filled with contrast fluid via the distal delivery catheter 16, whereupon the intended metal spiral 11 is inserted into the delivery catheter 21 and is fed in until it rolls itself up inside the distal balloon $6^1$. In a corresponding way, the proximal balloon $6^2$ is filled with contrast fluid in order to enable the parts to be visible via roentgen or other imaging means inside the body during the work to move them into position. After that a metal spiral 12 is also delivered to the proximal balloon $6^2$, as is shown in FIG. 3. When the metal spirals 11, 12, or like stiffening functioning means are located in the correct position, they are released by backing the constraining mandrins out of the metal spirals 11, 12. The contrast fluid 22, 23 is evacuated out from the balloons $6^1$, $6^2$ and the distal part 14 of the locking mechanism is pulled through its proximal ring 14B in the locking position. The conductor 20 is then pulled out accompanied by the inner sheath 15, which now runs freely and is pulled out from the distal balloon attachment and also the outer enclosing delivery sheath 24.

The embodiment which is shown in FIGS. 7–10 departs from the above described first embodiment, foremost by instead of using metal spirals as dispersing force which maintains a balloon or other occluding sail in position, it instead utilizes the rotating quality of non-bendable metals when they are compressed, and when the ends move past a critical point. For this object, there are thin nitinol threads attached around an inner core of material in each end inside a balloon according to the above. The distal and the proximal balloons have a further opening between them and the diameter of the balloon at its smallest part corresponding to the ASD-size, i.e. that it is somewhat but not much larger. The balloons are inflated by means of a contrast fluid whereupon the furthermost, as seen in the direction of insertion, attachment point of the nitinol threads are slowly pulled back at the same time as the nearest, as seen in the direction of insertion, are pushed ahead, i.e. in the direction toward each other. At a critical position, the threads twist or spiral sideways and maintain a circular shape, which desired shape is used according to the present invention. In position, the balloons are evacuated and the threads are locked in the twisted spring-like position.

More precisely, with reference to FIGS. 7–10 a device 101 is formed as an implant for closing a passage, for example, according to the above described embodiment, and which comprises a closing body 106 which is attachable at the passage, alone or in combination with further sealing means in a radial direction 107 which is also an expanding stiffening fluid tight closing body. The body 106 is arranged that after insertion through a body vein (not shown) in its longitudinal direction 150, it will be built up at the position 109 for the intended closing spot.

Figure 9A:
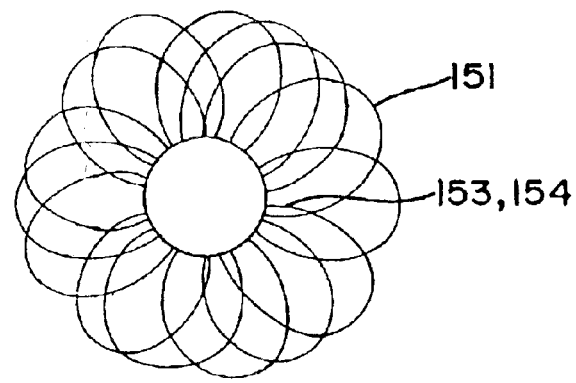
FIG. 9A shows an end view of the implant in its extended position.

A number of threads 151 which in the shown embodiment are eight in number, are arranged of such a material and with such qualities that they twist automatically sideways to form a circular or loop shape when compressed longitudinally, as is shown in FIG. 9, and are locked in the twisted, spiral or coil-like position for interconnecting the two chambers, and so on, against each other. The body 106 is preferably formed by a plurality of thin nitinol threads, or wires, which are attached respectively in axial direction 150, 152 relative to each other on movable holder nuclei 153, 154. The threads 151 are arranged to twist sideways in the same direction and then to assume a somewhat circular shape 155, similar to a flower, a propeller or an umbrella, with circular shape and arranged with suitable means for closing the passage. For example, the closing portion may be formed of layers of watertight material connected to the threads 151.

Figure 10:
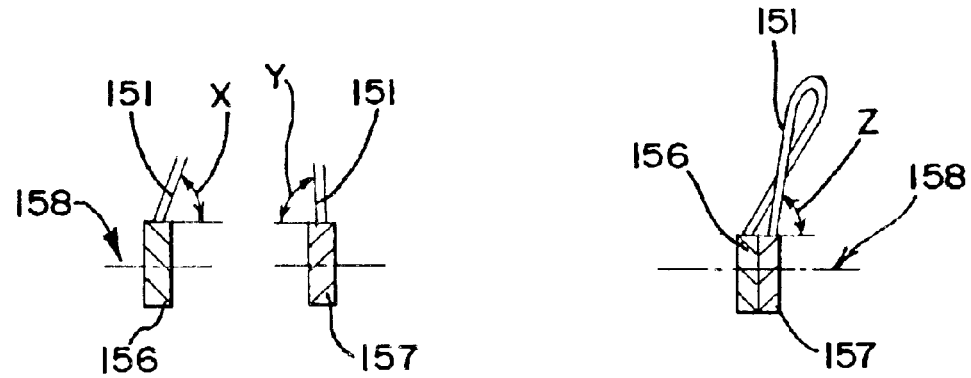

In the example according to FIG. 10 the threads 151 are shown attached with different inclination x, y with reference to the respective separate holder nuclei 156, 157. The threads 151 are arranged to be mutually forced to be directed toward that holder nucleus 157 from which the threads 151 depart with the largest angle y, as calculated from the center axis 158 of the holder nuclei, with similar angle z for the different threads 151.

FIGS. 11–16 further illustrate the foregoing embodiment of the present invention. FIG. 11 shows the implant 200 of the present invention in a perspective view in an initial position, i.e., before the device is applied to the passage in a circulatory system and deployed. In the figures a plurality of thin stiff generally inextensible, but somewhat flexible, members or wires 202 are provided. The members 202 may be nitinol and are more preferably biodegradable. Other materials for the members 202 include titanium and titanium alloys. While the figure shows eight members, it should be understood that the number of members can be varied and not change the spirit of the invention.

In one embodiment of the invention, the members 202 may be formed of a biodegradable or bioabsorbable material consisting of a polymer that exhibits a relatively high degree of biocompatibility. These materials have been previously used in stents, for example. Bioabsorbable implantable occlusive devices of the present invention may be made completely or partly of poly(alpha-hydroxy acid) such as polylactide [poly-L-lactide (PLLA), poly-D-lactide (PDLA)], polyglycolide (PGA), polydioxanone, polycaprolactone, polygluconate, polylactic acid-polyethylene oxide copolymers, poly(hydroxybutyrate), polyanhydride, polyphosphoester, poly(amino acids), or related copolymers materials, each of which have a characteristic degradation rate in the body. For example, PGA and polydioxanone are relatively fast-bioabsorbing materials (weeks to months) and PLA and polycaprolactone are relatively slow-bioabsorbing material (months to years). Reference is made to Enhancement of the Mechanical properties of polylactides by solid-state extrusion, W. Weiler and S. Gogolewski, Biomaterials 1996, Vol. 17 No. 5, pp. 529–535; and Deformation Characteristics of a Bioabsorbable Intravascular Stent, Investigative Radiology, December 1992, C. Mauli, Agrawal, Ph.D., P. E., H. G. Clark, Ph.D., pp. 1020–1024.

Mechanical properties of these materials generally increase with increasing molecular weight. For instance, the strength and modulus of PLA generally increase with increasing molecular weight. Degradation time generally decreases with decreasing initial molecular weight (i.e., a mesh device made of a low molecular weight polymer would be bioabsorbed before a mesh device made of a high molecular weight polymer). Low molecular weight PLA is generally more susceptible to thermo-oxidative degradation than high molecular weight grades, so an optimum molecular weight range should be selected to balance properties, degradation time, and stability. The molecular weight and mechanical properties of the material generally decrease as degradation progresses. PLA generally has a degradation time greater than 1 year. Ethylene oxide sterilization process (EtO) is a preferred method of sterilization. Furthermore, PLA has a glass transition temperature of about 60 degrees C., so care must be taken not to expose products to high temperature environments for substantial time periods (temperatures greater than 60 degrees C.), to avoid the possibility of dimensional distortion or other degradation effects.

PLA, PLLA, PDLA and PGA include tensile strengths of from about 40 thousands of pounds per square inch (ksi) to about 120 ksi; a tensile strength of 80 ksi is typical; and a preferred tensile strength of from about 60 ksi to about 120 ksi. Polydioxanone, polycaprolactone, and polygluconate include tensile strengths of from about 15 ksi to about 60 ksi; a tensile strength of about 35 ksi is typical; and a preferred tensile strength of from about 25 ksi to about 45 ksi.

PLA, PLLA, PDLA and PGA include tensile modulus of from about 400,000 pounds per square inch (psi) to about 2,000,000 psi; a tensile modulus of 900,000 psi is typical; and a preferred tensile modulus of from about 700,000 psi to about 1,200,000 psi. Polydioxanone, polycaprolactone, and polygluconate include tensile modulus of from about 200,000 psi to about 700,000 psi; a tensile modulus of 450,000 psi is typical; and a preferred tensile modulus of from about 350,000 psi to about 550,000 psi.

PLLA filament has a much lower tensile strength and tensile modulus than, for example, Elgiloy.RTM. metal alloy wire which may be used to make braided mesh devices or elements. The tensile strength of PLLA is about 22% of the tensile strength of Elgiloy.RTM. The tensile modulus of PLLA is about 3% of the tensile modulus of Elgiloy.RTM. mechanical properties and self-expansion are directly proportional to tensile modulus of the material. As a result, a PLLA filament or braided or woven element made to the same design as the implant of the present invention may have poor mechanical properties and may not be functional. The polymeric inextensible members 202 should have radial strength similar to metal members and should have the required mechanical properties capable of bracing open endoluminal or the like strictures.

Each member 202 has a proximal end 204 and a distal end 206. The proximal end 204 is shown here positioned adjacent the user's hand 208 while the distal end 206 enters the passage (not shown) first. In practice, of course, the hand would typically be much further away, given that the device will be introduced intravenously. The distal ends 206 of the inextensible members 202 are attached to a first holder 210 that has a ring shape like that of a circular hub or hub flange. The proximal ends 204 of the inextensible members 202 are attached to a second holder 212 similar to the first holder 210, i.e., a ring-shaped holder or hub.

At a point generally midway between the first holder 210 and the second holder 212 an expansible occluding body 214 is attached to the members 202. The occluding body 214 may be a generally circular, disc-shaped member, and may be made of a flexible fabric-like material consistent with surgical use and more preferably of a biodegradable material. The occluding body 214 has a distal face 216 oriented toward the distal ends 206 of the members 202 and a proximal face 218 oriented toward the proximal ends 204 of the members 202. The members 202 preferably have a thickened portion 220 where they pass through openings 222 in the occluding body 214. The thickened portion 220 is actually two parts 220a, 220b which serve to capture and mount the occluding body 214 therebetween.

The first holder 210 is attached to a first end 224 of a carrier rod 226 at the distal ends 206 of the members 202. The second holder 212 is slidably received on the carrier rod 226. In the condition shown in FIG. 11, the members 202 are arranged about the carrier rod 226 in a substantially equally spaced manner and generally aligned with the longitudinal axis A of the carrier rod 226. The occluding body 214 extends in a generally radial manner from the carrier rod 226 at a mid-point between the proximal 204 and distal ends 206 of the inextensible members. In the arrangement shown in FIG. 11, the implant 200 forms an elongated apparatus or article that generally extends along longitudinal axis A. The elongate form of the implant 200 permits it to be tightly compressed and inserted through an intravenous delivery mechanism and in the form shown is referred to as being in the insertion condition.

In operation, a driving implement 228, (e.g., a plastic tube) can be placed over the carrier rod 226 in contact with the second holder 212. The driving implement 228 is slid along or moved toward the first substantially fixed holder 210 (i.e., toward the first end 224 of the carrier rod 226) along the carrier rod 226. Generally, as will be further described, when the driving implement 228 is moved toward the first holder 210 the two holders 210, 212 are driven relatively closer together, and the implant 220 is changed into a deployed condition.

FIGS. 12–15 show the implant 200 in a perspective view in various conditions of deployment. As can be seen in these figures, moving the two holders 210, 212 together at first tends to cause the inextensible members 202 at the distal end to assume a gently outwardly bowed configuration with respect to the longitudinal axis A of the carrier rod 226. This outwardly bowed configuration pulls the expansible occluding body 214 into a tensioned radial disk shape.

Further moving the driving implement 228 towards the first holder 210 along the carrier rod 226 causes a first portion 230 of the inextensible members 202 located between the first holder 210 and the occluding body 214, to assume a more bowed, almost semi-circular shape where the distal ends 206 of the members 202 attach to the first holder 210 in a nearly perpendicular direction with respect to the longitudinal axis A of the carrier rod 226. A second portion 232 of the inextensible members 202 at the proximal end tends to remain relatively parallel to the longitudinal axis A at first.

The inextensible members 202 are shown in FIG. 13 in a condition in response to yielding to further compression. As shown, the first portions 230 of the members 202 have started to twist or spiral about the carrier rod 226 forming a plurality of generally radial loops (with respect to the axis of the carrier rod). What then happens is that the first portion 230 then passes through a critical point, whereupon each wire in this portion 230 snaps into a generally radially-extending loop, yielding a somewhat concave petal-shaped structure at the distal side of the occluding body 214. Further compressing the second portion 232 likewise results in the formation of similar loops in a petal-shaped structure on the proximal side of the occluding body 214.

FIGS. 14 and 15 show the implant 200 in a perspective view in a fully deployed condition. Both the first portion 230 and second portion 232 have responded to the compressing motion by twisting away from the axial direction A. Thereby, the first portion 230 of the members have resolved into a first fixation structure 230' adjacent the distal face 216 of the occluding body. Similarly, the second portion 232 of the members 202 have resolved into a second fixation structure 232' adjacent the proximal face 218 of the occluding body 214. The overlapping spiral shape of both the first and second fixation structure 230', 232' is a stable shape, that locks the implant 200 into a stable occluding or deployed condition upon the locking holders 210, 212 being driven together by the driving implement 228, as shown in FIG. 15.

FIG. 16 shows a perspective view of a portion of the implant without the occluding body and members or carrier rod. Thus, the first and second holders or hubs 210, 212 may be seen in more detail. The first and second holders 210, 212 may be adapted to be placed onto the carrier rod (not shown) by hollow central shafts 234, 236. Located about the central shafts 234, 236 are annular portions 238, 240 with a plurality of slots 242 or attachment points sized to fixedly receive the ends of the members 202. The slots 242 may extend to the periphery 244 of the annular portions 238, 240 to allow the members 202 to move from a longitudinal orientation to a radial orientation.

An extending tooth 246 may be formed on one of the first and second holders 210, 212 or in the alternate, the carrier rod (not shown) to engage and form a locking element with a corresponding recess (not shown) formed in one or both of the first and second holders 210, 212. In this manner, the implant 200 becomes locked into a fully deployed or final occluding condition upon being driven together by the driving implement by engagement of the tooth 246 and the recess.

The invention has been carefully described in the above-mentioned examples, and therefore the idea should be clearly understood that the invention is neither limited to the above described and on the drawings shown embodiment, but may be varied within the scope of the claims without departing from the concept of the invention.

What is claimed is:

1. An implant for occluding a passage in a circulatory system, comprising:
   a plurality of thin stiff members each having a proximal and a distal end;
   a first holder to which the distal ends of said members are attached;
   a second holder to which the proximal ends of said members are attached;
   an expansible occluding body attached to said members at a point intermediate said first and second holders, said occluding body having a distal and proximal face;
   wherein one or more of said plurality of members, said first holder, said second holder and said expansible occluding body is made of at least some biodegradable material;
   a carrier rod releasably attached to said first holder and upon which said second holder is slidably received;
   said plurality of members with said occluding body forming an elongated article extending along a longitudinal axis and being adapted for insertion through an intravenous delivery mechanism in an insertion condition;
   a driving implement on said carrier rod, said driving implement contacting said second holder and movable toward said first holder along said carrier rod;
   said members being attached to said first and second holders in a manner to cause said members to execute a twisting motion relative to said axis to yield a plurality of generally radially extending loops combining to form a first fixation structure adjacent said distal face of said occluding body, and a second fixation structure of generally radially extending loops adjacent said proximal face of said occluding body, said first and second fixation structures being fixed in a final occluding condition upon being driven together by said driving implement.

2. The implant of claim 1 wherein said plurality of members are formed completely of said biodegradable material.

3. The implant of claim 1 wherein said plurality of members and said expansive occluding body are formed completely of said biodegradable material.

4. The implant of claim 1 wherein said biodegradable material is one or more of PLLA, PDLA, PGA, polydioxanone, polycaprolactone, polygluconate, polylactic acid-polyethylene oxide copolymers, polyhydroxybutyrate, polyanhydride, polyphosphoester and poly amino acids.

5. The implant of claim 1 further comprising a locking element fixing said first and second fixation structures in a final occluding condition upon being driven together by said driving implement.

6. The implant of claim 1 wherein said locking element comprises an extending tooth located on one of said first and second holders which engages with a corresponding recess formed in the other of said first and second holders upon being driven together by said driving implement.

7. The implant of claim 1 wherein said members are attached to said first holder at a first angle of inclination relative to said axis and said members are attached to said second holder at a second angle of inclination which is different from said first angle.

8. The implant of claim 1 wherein said twisting motion causes said members attached to said first holder to initially bulge radially outwardly and then snap into an inverted condition having a concave shape for said radially extending loops of said first fixation structure, with the concavity facing said first holder.

9. The implant of claim 1 wherein said members are generally inextensible and have a thickened portion where said members attach to said expansible occluding body.

10. The implant of claim 1 wherein each said first and second holders include a hollow central shaft portion and an annular hub portion positioned about the central shaft portion.

11. The implant of claim 10 wherein each said annular hub portion includes a plurality of slots adapted to respectively receive one of said proximal and distal ends of said members.

12. The implant of claim 11 wherein each of said slots extend to an outer periphery of said annular hub portions of said first and second holders to permit said inextensible members to pivot from a first orientation generally parallel to said longitudinal axis to a second orientation generally radial with respect to said longitudinal axis.

13. A method for occluding a passage in a circulatory system, comprising:

providing an implant having a plurality of thin generally inextensible members each having a proximal and a distal end, with a first holder to which said distal ends of said members are attached, a second holder to which said proximal ends of said members are attached, an expansible occluding body attached to said members at a point intermediate said first and said second holders, said occluding body having a distal and proximal face, said plurality of members with said occluding body forming an elongated article extending along a longitudinal axis and being adapted for insertion through an intravenous delivery mechanism in an insertion condition;

mounting said implant on a carrier rod releasably attached to said first holder, and upon which said second holder is slidably received;

inserting said implant mounted on said carrier rod through said intravenous delivery mechanism into place at a passage to be occluded;

driving said holders relatively toward one another;

said members being attached to said first and second holders in a manner to thereby cause said members when being driven toward one another to execute a twisting motion relative to said axis to yield a plurality of generally radially extending loops combining to form a first fixation structure adjacent said distal face of said occluding body, and a second fixation structure of generally radially extending loops adjacent said proximal face of said occluding body, with said occluding body being thereby positioned in a final occluding condition; and permitting said members to biodegrade while in said final occluding condition and while occluding the passage to be occluded.

14. The method of claim 13 wherein said members are attached to said first holder at a first angle of inclination relative to said axis and said members are attached to said second holder at a second angle of inclination which is different from said first angle, and wherein said twisting motion causes said members attached to said first holder to initially bulge radially outwardly and then snap into an inverted condition having a concave shape for said radially extending loops of said first fixation structure, with the concavity facing said first holder.

15. An implant for occluding a passage in a circulatory system, comprising: a plurality of thin stiff members each having a proximal and a distal end; a first holder to which the distal ends of said members are attached; a second holder to which the proximal ends of said members are attached; an expansible occluding body attached to said members; said plurality of members with said occluding body forming an elongated article extending along a longitudinal axis and being adapted for insertion through an intravenous delivery mechanism in an insertion condition;

said members being attached to said first and second holders and a distance between said holders being reduceable in a manner to cause said members to execute a twisting motion relative to said longitudinal axis to yield a plurality of generally radially extending loops forming at least one fixation structure, thereby expanding the occluding body, and said at least one fixation structure being fixable in a final occluding condition, wherein one or more of said plurality of stiff members, said first holder, said second holder and said expansible occluding body is made of at least some biodegradable material.

16. The implant of claim 15 wherein the entirety of said implant remaining in the body is biodegradable.

* * * * *